US00PP12889P2

(12) United States Plant Patent
Lamb et al.

(10) Patent No.: US PP12,889 P2
(45) Date of Patent: Aug. 27, 2002

(54) SPATHIPHYLLUM PLANT NAMED 'FLORIDA BEAUTY'

(75) Inventors: Ann E. Lamb, Sebring; David R. Lilly, Boynton Beach; Randy L. Allamand, Lake Placid, all of FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 66 days.

(21) Appl. No.: 09/699,490

(22) Filed: Oct. 31, 2000

(51) Int. Cl.[7] ..... A01H 5/00

(52) U.S. Cl. ..... Plt./364

(58) Field of Search ..... Plt./364

*Primary Examiner*—Bruce R. Campell
*Assistant Examiner*—Annette H. Para
(74) *Attorney, Agent, or Firm*—Foley & Lardner

(57) ABSTRACT

A new Spathiphyllum plant named 'Florida Beauty' characterized by its large size and its large, elliptic, white spathes which are held well-above the foliage. The foliage of 'Florida Beauty' is dark-green, glossy and supple. Plants of 'Florida Beauty' are easy to grow and are tolerant of temperature extremes without damage to the foliage. The new cultivar is particularly well-adapted to, and durable in, indoor/interior scape conditions.

3 Drawing Sheets

BACKGROUND OF THE INVENTION

The present invention comprises a new and distinct cultivar of Spathiphyllum plant, botanically known as *Spathiphyllum hybrid*, and hereinafter referred to by the cultivar name 'Florida Beauty'.

The new cultivar is the product of a breeding program carried out by the inventors, Ann E. Lamb, David R. Lilly and Randy L. Allamand. The new cultivar named 'Florida Beauty' is the result of a cross made in Apopka, Fla. in November of 1993. The female or seed parent was the cultivar Spathiphyllum 'Lynise' (U.S. Plant Pat. No. 6,145). The male parent was a unique seedling, found among seedling-derived Spathiphyllum 'Mauna Loa', named 'Vibrant' (unpatented), which was selected and maintained by the inventors and used only for breeding purposes.

The new cultivar named 'Florida Beauty' was discovered and selected by the inventors from a group of seedlings of the stated cross in Homestead, Fla. on May 16, 1996. Propagation by tissue culture, in Sebring, Fla., under the supervision of the inventors, was used to increase the number of plants for evaluation and has demonstrated the stability of the combination of characteristics as herein described from generation to generation.

BRIEF DESCRIPTION OF THE INVENTION

The following traits have been repeatedly observed and are determined to be basic characteristics of 'Florida Beauty' which in combination distinguish this Spathiphyllum as a new and distinct cultivar:

1. Plants are large, upright and ideally suited for pot sizes 25 cm or larger;

2.Leaves are dark-green, glossy and leathery with a wavy margin. The leaf blade is broad and textured;

3. Spathes are white, elliptic, cupped and held above the foliage on thick, sturdy peduncles; and 4. Plants are easy to grow and are tolerant of temperature extremes (108° F.–52° F.) without foliar damage.

'Florida Beauty' has not been observed under all possible environmental conditions. The phenotype of the new cultivar may vary significantly with variations in environment such as temperature, light intensity, and daylength, without any change in genotype.

Of the commercial cultivars known to the present inventors, the most similar in comparison to 'Florida Beauty' are the parental cultivar 'Lynise' and the cultivar Spathiphyllum 'Aziza' (U.S. Plant patent application Ser. No. 09/586,604). In comparison to 'Lynise', 'Florida Beauty' has pure white flowers while the flowers of 'Lynise' are cream-white in color. Plants of 'Florida Beauty' are larger than plants of 'Lynise'. The leaves of 'Florida Beauty' are darker-green, wider, shinier and thicker than the leaves of 'Lynise'.

In comparison to 'Aziza', the inflorescence of 'Florida Beauty' is held higher above the foliage than the inflorescence of 'Aziza'. The leaves of 'Florida Beauty' are supple and less rigid than the leaves of 'Aziza'. Plants of 'Florida Beauty' produce fewer side branches than plants of 'Aziza'.

BRIEF DESCRIPTION OF THE DRAWINGS

The accompanying color photographic illustrations show typical characteristics of a 12-month-old plant of 'Florida Beauty' grown in a 25-cm pot initiated from two microcuttings obtained by tissue culture and grown under appropriate growing conditions, with colors being as nearly true as possible with illustrations of this type.

Sheet 1 is a side view showing the inflorescence and foliage of 'Florida Beauty'.

Sheet 2 is a close-up view of the upper leaf surface.

Sheet 3 is a close-up view of the lower leaf surface.

DETAILED BOTANICAL DESCRIPTION

The following observations, measurements and values describe 12 month old plants (3 month old liner and 9 month finishing time), finished in 25 cm pots and grown in Homestead, Fla. under greenhouse conditions which closely approximate those generally used in horticultural practice. All color references are measured against The Royal Horticultural Society (R.H.S.) Colour Chart. Colors are approximate as color depends on horticultural practices such as light level and fertilization rate, among others, without, however, any variance in genotype.

Classification:

*Commercial.*—*Spathiphyllum hybrid* cv. 'Florida Beauty'.

Parentage:

*Male parent.*—Selection of Spathiphyllum 'Mauna Loa' named 'Vibrant'.

*Female parent.*—Spathiphyllum 'Lynise'.

Propagation: Vegetative, by tissue culture or division.

Plant: Under appropriate growing conditions, plant attains a size of approximately 66 cm to 75 cm in height and approximately 85 cm to 98 cm in width.

Leaves:

*Form.*—The leaf blade is elliptic with a cuneate to obtuse base and a cuspidate to acute apex which curves downward. The margins are entire and slightly wavy. The midrib is straight over approximately ⅔ the length of the leaf and curved downward somewhat toward the leaf tip. The leaves are moderately thick, leathery and supple. The leaf surface is textured and glossy.

*Size.*—Leaf blades are approximately 33 cm to 36 cm in length and approximately 16.5 cm to 19 cm in width.

*Petiole.*—The petiole is approximately 40 cm to 44 cm in height from the base of the petiole to the base of the leaf blade on primary shoots. Secondary shoots are smaller depending on the age of the shoot. The petiole is approximately 8 mm in diameter at the junction of the geniculum and petiole sheath. The petiole below the geniculum is straight.

*Petiole sheath.*—The petiole sheath is approximately 33 cm to 38 cm in length and approximately 14 mm to 17 mm in width at the midpoint. The tip of the petiole sheath is oblique and bluntly rounded. The petiole sheath terminates approximately 1 cm from the base of the geniculum, or at the base of the geniculum.

*Geniculum.*—The geniculum is approximately 6.0 cm to 7.0 cm in length and approximately 1 cm in diameter. The color is greener than, but closest to, RHS 147B.

*Veins.*—Veins are sunken, and the leaf blade is convex between veins on the upper surface giving the leaf a textured appearance. The midrib is sunken. Well-defined primary veins radiate out from the midrib over the length of the leaf. There are approximately 15 pairs of primary veins on the leaf.

*Color.*—Leaf: Upper surface: RHS 139A. Lower surface: RHS 146B to RHS 147B. Midrib: Upper surface: RHS 137A. Lower surface: RHS 146D. Petiole: Darker and greener than, but closest to, RHS 137A. Petiole sheath: Darker and greener than, but closest to, RHS 137A.

Inflorescence:

*Immature.*—The spathe is tightly rolled around the spadix and emerges from the petiole sheath. The spathe is fully open approximately at the time the peduncle is fully elongated—approximately 95 cm to 101 cm above the soil surface, measured at the tallest point. The peduncle is approximately 68 cm to 75 cm in length measured from the crown of the plant to the base of the spathe. It is approximately 8 mm in diameter measured at the midpoint of the peduncle. The peduncle is darker and greener than, but closest to, RHS 146B.

*Mature.*—Spathe: Size: The spathe is approximately 26.0 cm to 29 cm long and approximately 12.0 cm to 15.2 cm wide. Color: Fully open: Adaxial surface: Pure white, RHS 155D, tinged with RHS 148D along the midrib. Abaxial surface: Pure white, RHS 155 D. Midrib (abaxial): Darker and greener than, but closest to RHS 146B. Apex: RHS 146B. Faded: Adaxial surface: RHS 155D streaked with RHS 146B. Abaxial surface: RHS 155D streaked with RHS 146B. Midrib: Darker than, but closest to, RHS 146B. Apex: RHS 146B.

*Arrangement.*—The spathe terminates as a straight peduncle which opens vertically above the leaves.

*Shape.*—The spathe is elliptic with a cuneate to obtuse base and an acute or cuspidate twisted apex.

*Flowering.*—Depending on season, approximately 3 inflorescences will be present on plants; smaller, narrower blossoms may occur on less mature growth.

*Lastingness of the individual inflorescence.*—Spathes begin to change from pure white to white streaked with green after about 3 to 4 weeks, becoming almost entirely green after about 6 weeks. Cut flowers last about 7 days off the plant.

Floral organs:

*Spadix.*—Size: Approximately 12.5 cm in height and approximately 2 cm in width. Color: When the spathe unrolls, the spadix is yellow, RHS 19C, gradually changing to darker and greener than, but closest to, RHS 146B as the flower fades. Stamens: Anthers and filaments are minute and not clearly visible. Pollen: RHS 158D. Pistil: RHS 19C in color, conical, protruding between the staminate flowers, fixed to the main axil. The pistillate flowers extend approximately 3 mm beyond the staminate flowers.

*Seeds.*—Approximately 2 mm long, reniform in shape, light to medium brown color. Surface texture of seed coat is pitted; each individual capsule contains approximately 1 to 6 seeds. Depending on size and degree of pollination, a single inflorescence can yield over 800 seeds.

*Fruit.*—Oblong to elliptic berry, 9 mm long, 8 mm wide, green RHS 146 B with yellow RHS 19 C when ripe.

Roots: Thick white roots with fine laterals.

Pest/disease resistance/susceptibility: Preventative disease and pest control measures used to grow crops of 'Florida Beauty' are typical of ordinary commercial practice; 'Florida Beauty' has no particular sensitivity to common pests or pathogens.

We claim:

1. A new and distinct cultivar of Spathiphyllum plant named 'Florida Beauty', as illustrated and described.

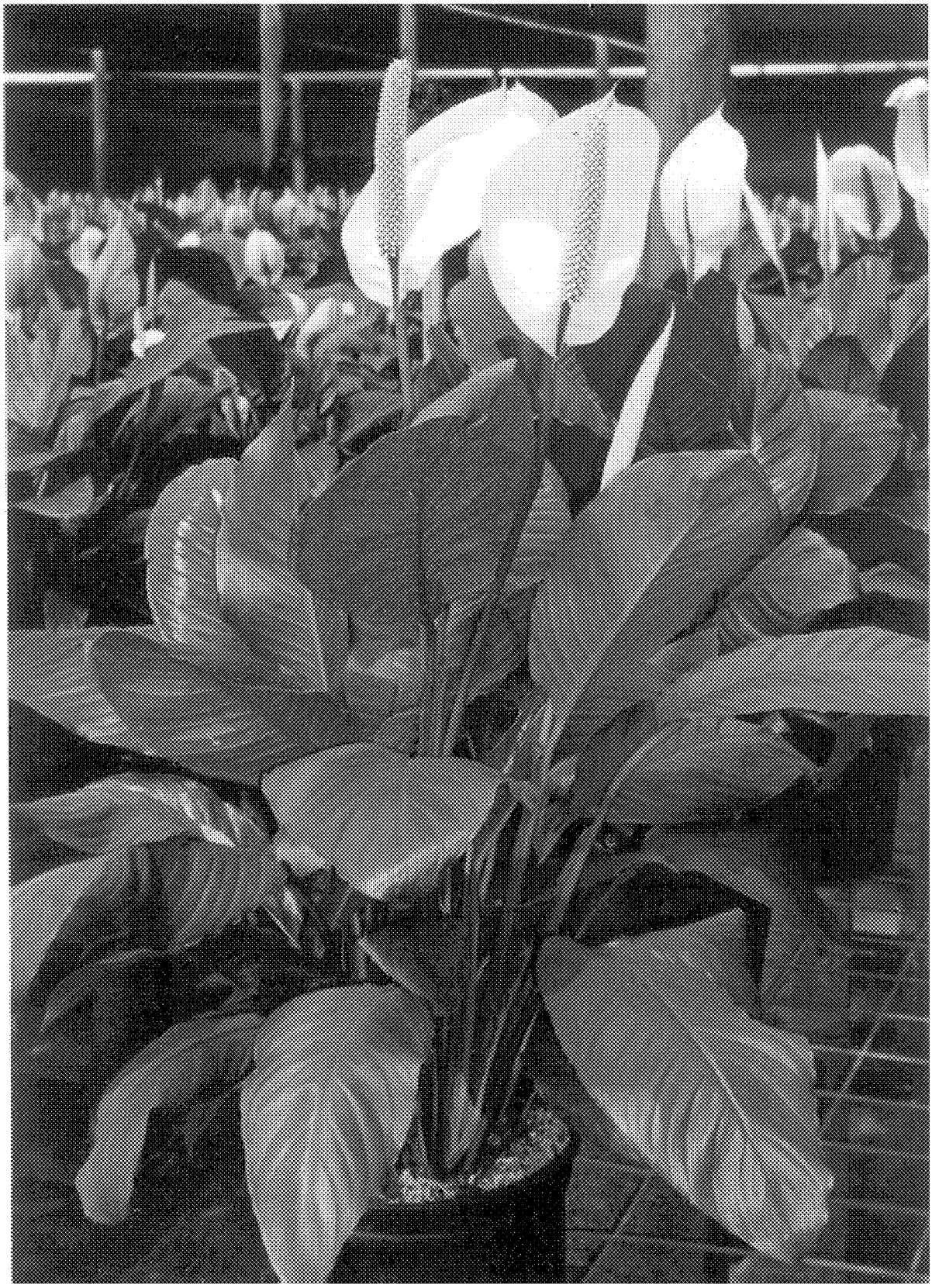

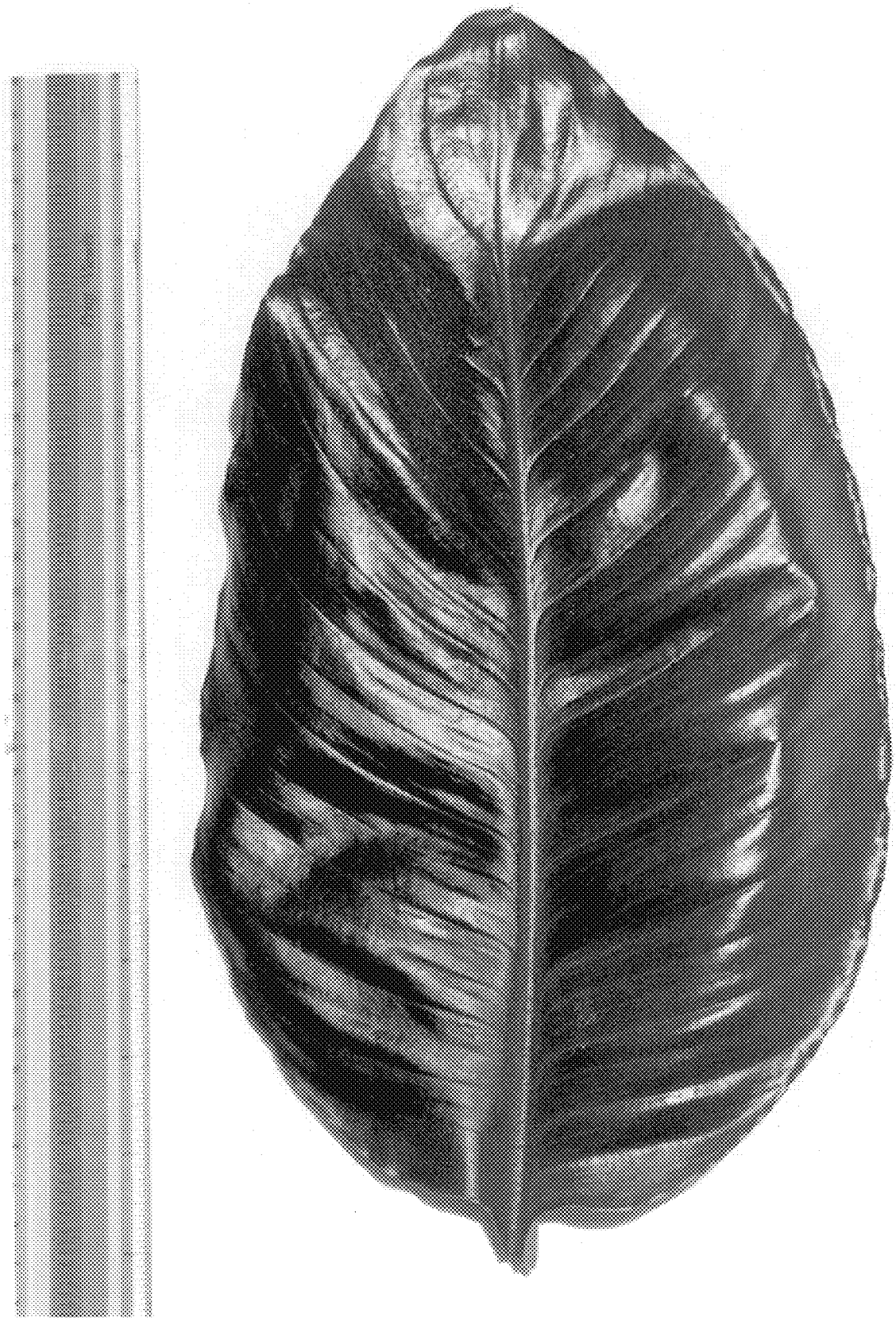

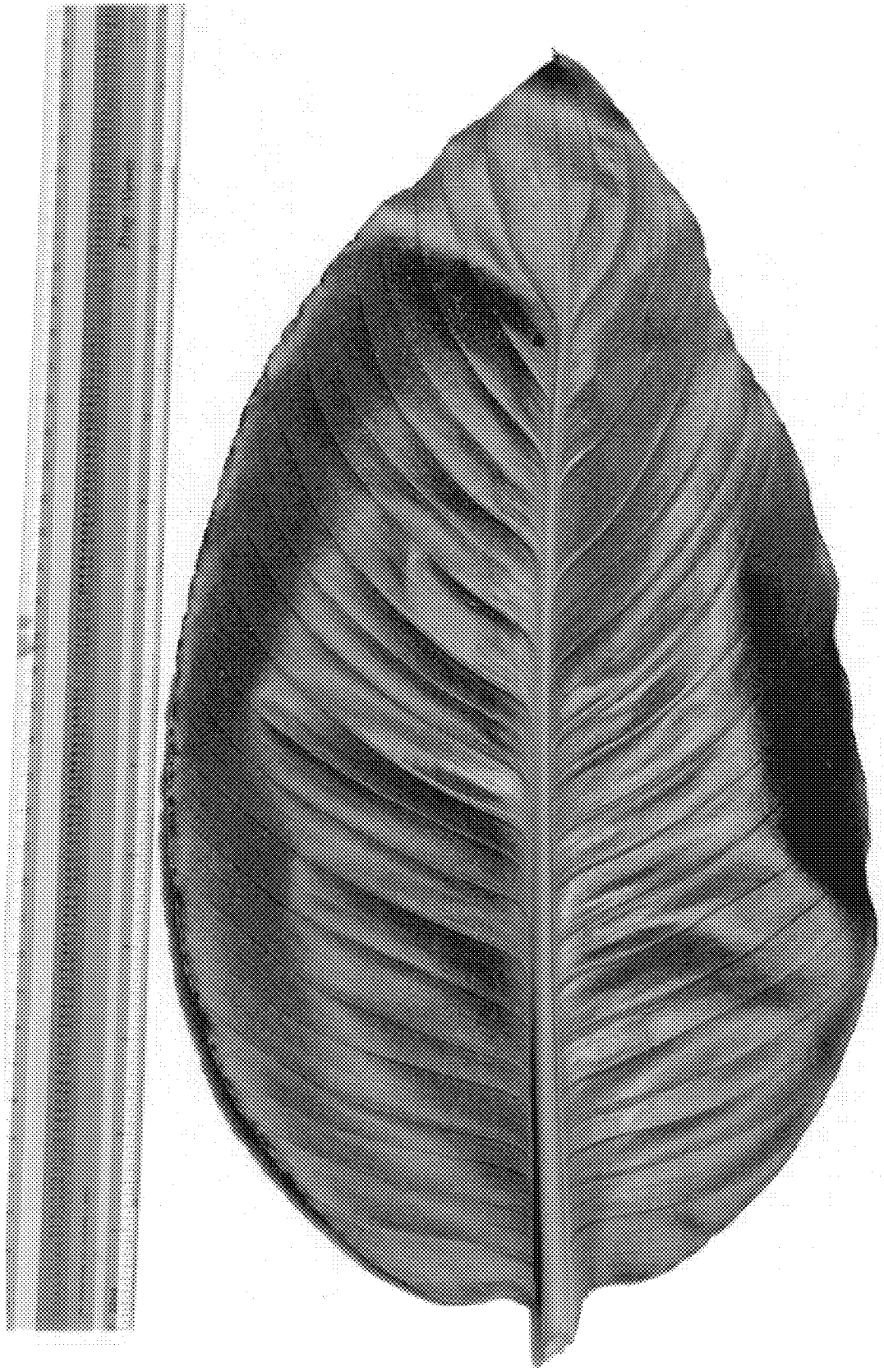

* * * * *